(12) United States Patent
Chappo (10) Patent No.: US 9,538,107 B2
(45) Date of Patent: Jan. 3, 2017

(54) IMAGING DETECTOR (71) Applicant: KONINKLIJKE PHILIPS N.V., Eindhoven (NL)

(72) Inventor: Marc Anthony Chappo, Elyria, OH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/890,598

(22) PCT Filed: May 7, 2014

(86) PCT No.: PCT/IB2014/061263
§ 371 (c)(1),
(2) Date: Nov. 12, 2015

(87) PCT Pub. No.: WO2014/184714
PCT Pub. Date: Nov. 20, 2014

(65) Prior Publication Data
US 2016/0094798 A1    Mar. 31, 2016

Related U.S. Application Data

(60) Provisional application No. 61/824,020, filed on May 16, 2013.

(51) Int. Cl.
*H04N 5/361* (2011.01)
*A61B 6/00* (2006.01)
(Continued)

(52) U.S. Cl.
CPC ............... *H04N 5/361* (2013.01); *A61B 6/032* (2013.01); *A61B 6/035* (2013.01); *A61B 6/4233* (2013.01);
(Continued)

(58) Field of Classification Search
CPC ........ H04N 3/155; H04N 5/361; G01T 1/2985
See application file for complete search history.

(56) References Cited

U.S. PATENT DOCUMENTS 5,812,191 A * 9/1998 Orava ................... G01T 1/2928
250/370.09
6,510,195 B1    1/2003 Chappo et al.
(Continued)

FOREIGN PATENT DOCUMENTS

| WO | 02/39900 | 5/2002 |
|---|---|---|
| WO | 2010/109354 | 9/2010 |
| WO | 2012/127403 | 9/2012 |

*Primary Examiner* — David Porta
*Assistant Examiner* — Faye Boosalis (57) ABSTRACT

A silicon imaging detector tile (216) includes a silicon photosensor layer (302) including a plurality of detector pixels (304), each with a photo-transistor (406), and a silicon electronics layer (314), coupled to the silicon photosensor layer, including a current-to-frequency converter and bias control (404) for each of the plurality of photo-transistor. A method includes sensing, with a photo-transistor of a detector pixel of a silicon photosensor layer of an imaging detector and in an absence of x-ray radiation, a dark current, regulating, with bias control, an amount of the dark current transmitted to a current-to-frequency converter of a silicon electronics layer coupled to the silicon photosensor layer, and converting, with the current-to-frequency converter, the amount of the dark current transmitted to the current-to-frequency converter.

23 Claims, 6 Drawing Sheets (51) Int. Cl.
  *G01T 1/20*    (2006.01)
  *H04N 5/32*    (2006.01)
  *H04N 5/3745*  (2011.01)
  *A61B 6/03*    (2006.01)
  *G01T 1/24*    (2006.01)
  *H04N 5/225*   (2006.01)
  *H04N 5/378*   (2011.01)

(52) U.S. Cl.
  CPC ............... *G01T 1/2018* (2013.01); *G01T 1/24* (2013.01); *H04N 5/2253* (2013.01); *H04N 5/32* (2013.01); *H04N 5/378* (2013.01); *H04N 5/37455* (2013.01); *A61B 6/4241* (2013.01)

(56) References Cited

U.S. PATENT DOCUMENTS

| | | |
|---|---|---|
| 2004/0099920 A1 | 5/2004 | Rossi et al. |
| 2005/0167603 A1 | 8/2005 | Hoffman |
| 2007/0221858 A1 | 9/2007 | Abenaim et al. |
| 2010/0116999 A1 | 5/2010 | Tumer et al. |
| 2012/0138774 A1* | 6/2012 | Kelly ............... G11B 20/00086 250/208.1 |

* cited by examiner (Prior Art)
FIG. 1

IMAGING DETECTOR

CROSS REFERENCE TO RELATED APPLICATIONS

This application is a national filing of PCT application Serial No. PCT/IB2014/061263, filed May 7, 2014, published as WO 2014/184714 A1 on Nov. 20, 2014, which claims the benefit of U.S. Provisional Application No. 61/824,020 filed May 16, 2013, which is incorporated herein by reference.

FIELD OF THE INVENTION

The following generally relates to an imaging detector and more particularly to an imaging detector with a silicon detector tile that includes a photo-transistor based detector pixel and electronics that utilizes the photo-transistor dark current as a bias for a current-to-frequency converter. Signals generated by the photo-transistor are converted into digital signals in the detector which is described in connection with computed tomography (CT).

BACKGROUND OF THE INVENTION

A CT scanner has included a detection system with an array of photodiode based detector pixels and processing electronics for each detector pixel with an analog-to-digital (A/D). The A/D converter has been employed as a current-to-frequency (I/F) converter that generates a train of pulses with a pulse frequency indicative of an input of photons incident on a detector pixel. Examples of such a converter are described in U.S. Pat. No. 6,671,345 B2 Vrettos et al., filed Nov. 7, 2001, and entitled "Data Acquisition for Computed Tomography," which is incorporated herein by reference in its entirety, and "A New 2D-Tiled Detector for Multislice CT," Luhta et al., Medical Imaging 2006: Physics of Medical Imaging, Vol. 6142, pp. 275-286 (2006).

Figure 1:
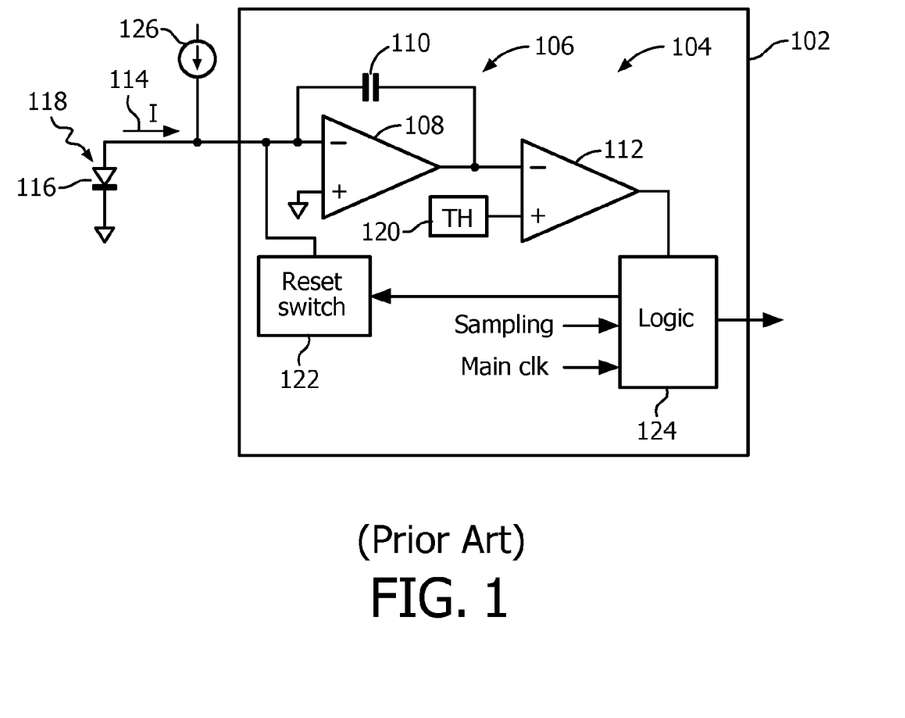
FIG. 1 schematically illustrates a prior art imaging detector that includes a photodiode based detector pixel, processing electronics with an I/F converter, and a current source to generate a bias current for the I/F converter.

FIG. 1 illustrates an example in which processing electronics 102 include an A/D converter 104 employed as an I/F converter. The A/D converter 104 includes an integrator 106 (an amplifier 108 and an integrating capacitor 110 in this example) and a comparator 112. The integrator 106 integrates, each integration period, current "I" 114 produced by a photodiode based detector pixel 116 in response to radiation 118 impinging on a scintillator of a photodiode based detector pixel 116. The comparator 112 compares the output of the integrator 106 with a preset threshold (TH) 120 and generates a pulse only when the output satisfies the threshold 120. A reset switch 122 resets the integrator 106 in response to the generation of a pulse.

In FIG. 1, digital logic 124 controls the reset switch 122, including closing the reset switch 122 to reset the integrator 106 and opening the reset switch 122. The digital logic 124 also processes the output of the comparator 112. In one instance, this includes counting a number of pulses output by the comparator 112 and determining a time from a first pulse of the integration period to a last pulse of the integration period. From this data, the digital logic unit 124 can generate an output signal indicative of the frequency of the pulses (e.g., number of pulses in an integration period/the time between the first and last pulses in the integration period), which is indicative of the current or charge per unit of time of the detected radiation.

The integrator 106 also integrates, each integration period, a bias current supplied to the integrator 106 input by a bias current source 126. The bias current is required to ensure that at least one pulse occur within each integration period (i.e., in the absence of any detected photons and thus a signal from the detector pixel 116) so that a frequency can be determined by the A/D converter 104. However, the current source 120 introduces electronic noise into the input of the A/D converter 104, which may increase the noise floor, relative to a configuration without the current source 120, and, hence, raise the lower limit of dose levels for lower dose scanning applications to dose levels that result in signals that are above the noise floor.

In the current state of the art of CT detectors, phototransistors are not used due to dark current limitations of electronics noise and variations with temperature and accumulated radiation dose.

SUMMARY OF THE INVENTION

Aspects described herein address the above-referenced problems and/or others.

The following describes an imaging detector that includes photo-transistor based detector pixels and bias control that utilizes a dark (electrical) current produced by the photo-transistors, in the absence of x-ray radiation, to bias current-to-frequency (I/F) converters that convert electrical current signals produced by the photo-transistors into digital signals. The inherent gain of a photo-transistor improves the signal to noise ratio (SNR), while utilizing the dark current as the I/F converter bias current keeps the electronic noise level equal to using a current source to produce the bias current. Such an imaging detector is well-suited for low dose imaging applications at least due to inherent gain of the phototransistor. Additionally, the phototransistor can enable photon counting detection when interfaced with an appropriate circuit contained in the electronics portion of the detector.

In one aspect, an imaging detector includes a silicon photosensor layer including a plurality of detector pixels, each with a photo-transistor and a silicon electronics layer, coupled to the silicon photosensor layer, including a current-to-frequency converter and bias control for each of the plurality of photo-transistors.

In another aspect, a method includes sensing, with a photo-transistor a of detector pixel of a silicon photosensor layer of an imaging detector and in an absence of x-ray radiation, a dark current, regulating, with bias control, an amount of the dark current transmitted to a current-to-frequency converter of a silicon electronics layer coupled to the silicon photosensor layer, and converting, with the current-to-frequency converter, the amount of the dark current transmitted to the current-to-frequency converter.

In another aspect, an imaging system includes a radiation source that emits radiation, a detector array that detects the radiation and generates a digital signal, and reconstructor that reconstructs the digital signal, generating volumetric image data. The detector array includes a plurality of detector tiles, each detector tile including a silicon photosensor layer with a plurality of detector pixels, each detector tile including a photo-transistor, and a silicon electronics layer, coupled to the silicon photosensor layer, including a current-to-frequency converter and bias control for each of the plurality of photo-transistor. The current-to-frequency converter converts a signal from the photo-transistor into the digital signal.

The invention may take form in various components and arrangements of components, and in various steps and arrangements of steps. The drawings are only for purposes of illustrating the preferred embodiments and are not to be construed as limiting the invention.

DETAILED DESCRIPTION OF EMBODIMENTS

Figure 2:
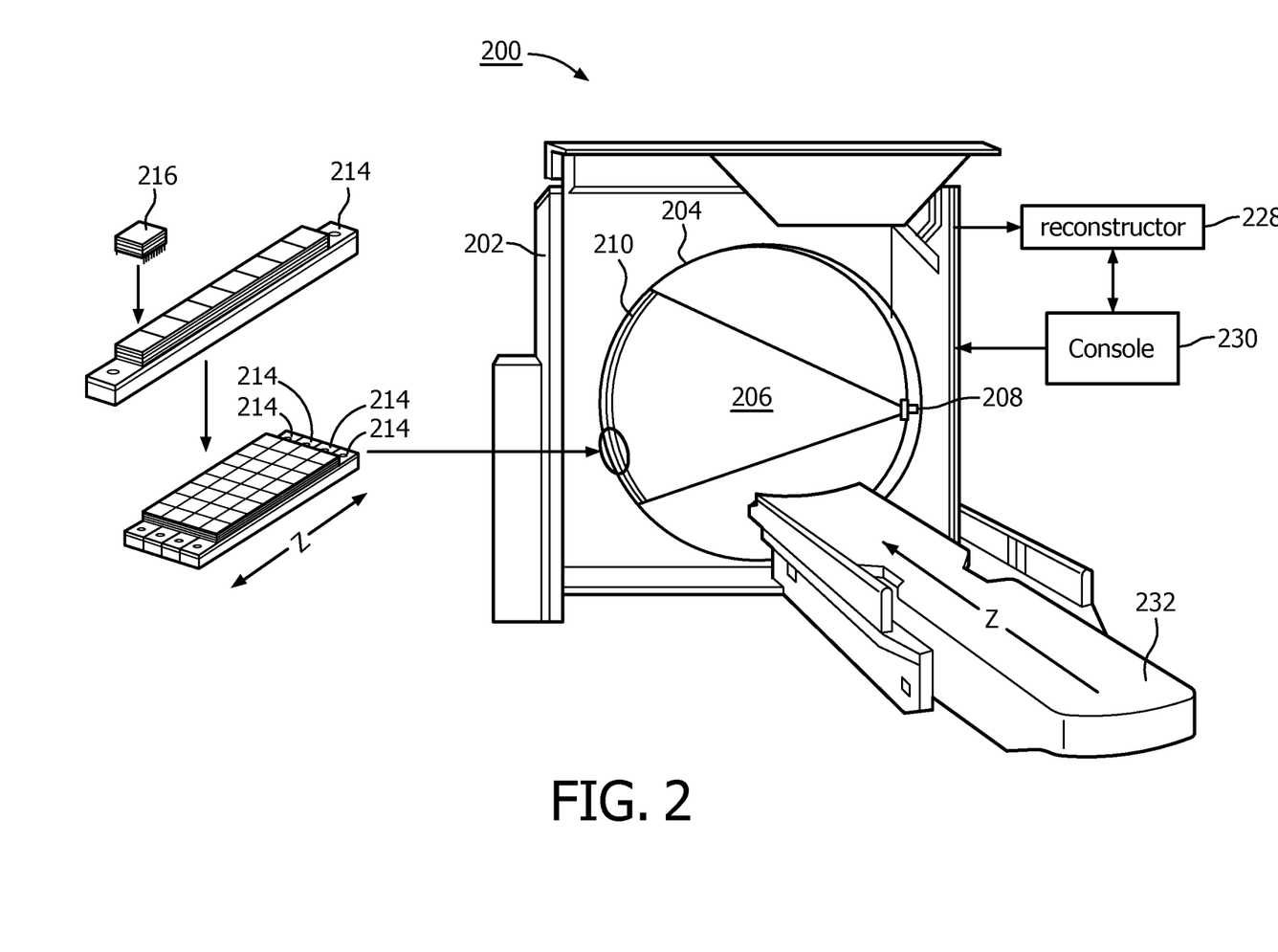
FIG. 2 schematically illustrates an example imaging system with detector tiles that include photo-transistor arrays with photo-transistor based detector pixels and processing electronics that utilize the dark current of photo-transistors to bias corresponding I/F converters of the processing electronics.

FIG. 2 illustrates an imaging system 200 such as a computed tomography (CT) scanner. The imaging system 200 includes a generally stationary gantry 202 and a rotating gantry 204. The rotating gantry 204 is rotatably supported by the stationary gantry 202 and rotates around an examination region 206 about a longitudinal or z-axis. A radiation source 208 such as an x-ray tube is supported by the rotating gantry 204 and emits radiation that traverses the examination region 206.

A radiation sensitive detector array 210 subtends an angular arc opposite the radiation sources 208 across the examination region 206. In the illustrated embodiment, the radiation sensitive detector array 210 includes a plurality of detector modules 214 arranged with respect to each other along a direction transverse to the z-axis. A detector module 214 includes a plurality of silicon detector tiles 216 arranged with respect to each other along the z-axis. Each silicon detector tile 216 detects radiation traversing the examination region 206 and generates electrical signals indicative thereof.

As described in greater detail below, each tile 216 includes a plurality of photo-transistor based detector pixels, forming a photo-transistor array (PTA) for each tile, and processing electronics with a current-to-frequency (I/F) converter (e.g., similar to the I/F converter discussed in connection with FIG. 1) and bias control for each photo-transistor in which the bias control utilizes a dark (electrical) current produced by the photo-transistor, in the absence of x-ray radiation, to bias the I/F converter so that at least one pulse occurs within each integration period so that a frequency can be determined by the I/F converter.

A reconstructor 228 reconstructs the signals from the silicon detector tiles 216 and generates volumetric image data indicative thereof. An image processor or the like can generate one or more images based on the image data. A computing system or other computer serves as an operator console 230. Software resident on the console 230 allows the operator to control the operation of the system 200. A patient support 232, such as a couch, supports an object or subject such as a human patient in the examination region 206.

A non-limiting example of the silicon detector tile 216 is described next.

Figure 3:
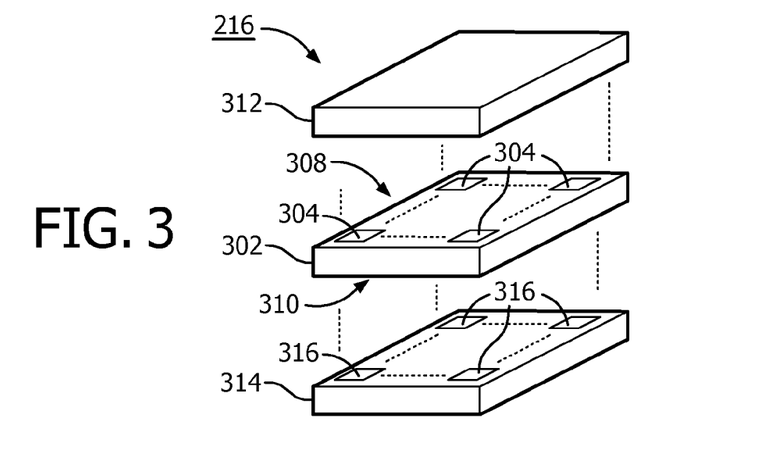
FIG. 3 schematically illustrates an example of the detector tile of FIG. 2.

In one instance, the detector tile 216 is substantially similar to and/or based on the detector tile described in U.S. Pat. No. 6,510,195B1 to Chappo et al, filed Jul. 28, 2001, and entitled "Solid State X-Radiation Detector Modules and Mosaics thereof, and an Imaging Method and Apparatus Employing the Same," which is incorporated herein by reference in its entirety. Other detector array arrangements, including combinations with and/or based on the above, are also contemplated herein. FIG. 3 illustrates an example of the silicon detector tile 216.

In FIG. 3, the silicon detector tile 216 includes the silicon photosensor layer 302, which includes a plurality of photosensitive areas 304 on a first side 308 of the photosensor layer 302. The illustrated silicon photosensor layer 302 is a back-illuminated photosensor with electrodes (not visible) that inter-connect the photosensitive areas 304 to bonding pads or the like (not visible) located on a second opposing side 310 of the photosensor 302. In a variation, the photosensor 302 can be a front-illuminated photosensor with vias that route the signals from the first side 308 to the pads on the opposing side 310.

The silicon detector tile 216 further includes a scintillator layer 312. The scintillator layer 312 may be a single layer or include a plurality of scintillator pixels (pixelated). In the latter instance, the scintillator layer 312 may include a number of scintillator pixels corresponding to a number of photosensitive areas for a one to one relationship between scintillator pixel and photosensitive area 304. In yet another instance, different scintillator pixels may correspond to different sub-groups of the photosensitive areas 304. The scintillator layer 312 is optically coupled to the silicon photosensor 218.

Figure 4:
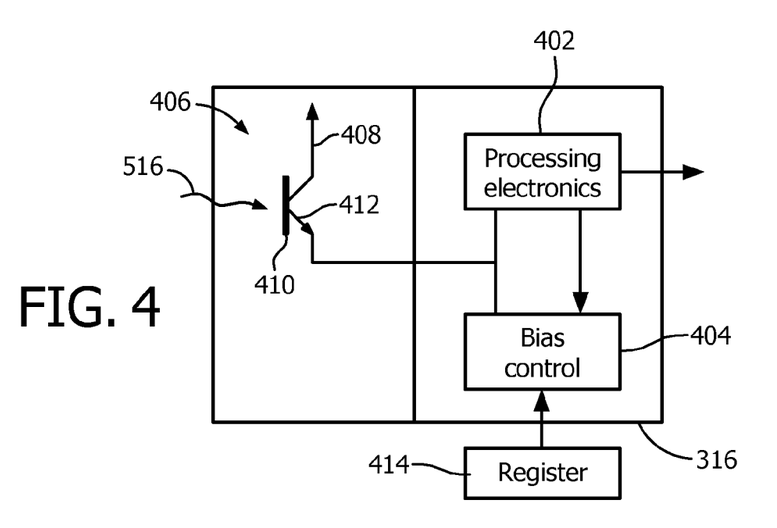
FIG. 4 schematically illustrates a single detector pixel/processing electronics pair of the detector tile of FIG. 3 with bias control logic in the silicon processing electronics layer.

The silicon detector tile 216 further includes a silicon electronics layer or substrate 314 with electronics areas 316. The electronics areas 316 are electrically coupled to the bonding pads of the photosensitive areas 304. FIG. 4 illustrates a photosensitive area 304/electronics area 316 pair. The electronics area 316 includes processing electronics 402 and bias control 404. As discussed herein, the processing electronics 402 includes an A/D converter that is employed as an I/F converter, which can be substantially similar to that described in connection with FIG. 1 and/or otherwise.

The illustrated photosensitive area 304 includes a photo-transistor 406 in FIG. 4. Collectively, the photo-transistors 406 of each tile 216 are referred to herein as a photo-transistor array (PTA). The photo-transistor 406 includes a collector 408, a base 410 and an emitter 412, which is in electrical communication with an input terminal of the processing electronics 402. When x-ray radiation is incident on the scintillator 312 (FIG. 3), light produced by the scintillator 312 in response thereto and indicative of an energy of the radiation drives the base 410, and the emitter current is an amplified base current.

Generally, each photo-transistor 406 can be thought of as a photodiode with a built in current amplifier in that a same amount of light and applied bias voltage produce a greater amount of output current. In the absence of the x-ray radiation, leakage current drives the base 410, and the emitter current is referred to as a dark (electrical) current. The bias control 404 regulates the amount of the dark current that is transmitted or fed to the processing electronics 402. In one instance, this includes allowing enough dark current so that at least one pulse occurs within each integration period so that a frequency can be determined by the I/F converter.

Various approaches can be utilized to control how much of the dark current is fed to the processing electronics 402 as the I/F converter bias current. For example, in one non-limiting instance, the bias control 404 utilizes a variable current sink to control how much of the dark current is fed to the processing electronics 402. In the illustrated example, a programmable register 414 includes bits that can be set to indicate a desired bias current for the processing electronics 402, and the bias control element 404 utilizes the register to regulate the dark current.

It is to be appreciated that by utilizing the dark current as such, the current source 126 of FIG. 1, which was used to produce the bias current for the I/F converter, can be omitted. As such, electronic noise produced by the current source 126, which would otherwise be present if the current source 126 was present, is traded for noise associated with PTA dark current, thereby allowing the PTA to replace the photodiode detector without any electronic noise increase.

Figure 5:
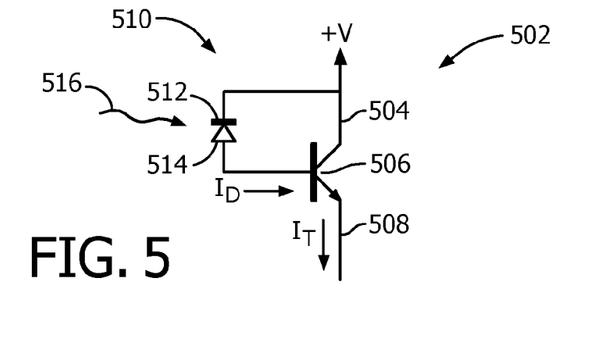
FIG. 5 schematically illustrates an example electrical circuit schematic representing the photo-transistor of the detector tile of FIG. 4.

FIGS. 5-8 show a progression of how a phototransistor includes a photodiode with transistor gain. FIG. 5 shows an electrical schematic representation of the photo-transistor 406 of FIG. 4, and FIGS. 6, 7 and 8 show semiconductor material based representations of the photo-transistor 406 of FIG. 4.

In FIG. 5, the photo-transistor 406 includes a transistor 502 (with a collector 504, base 506 and emitter 508) and a photodiode 510 (with a cathode 512 and an anode 514). The cathode 512 of the photodiode 510 is electrically connected to the collector 504 of the transistor 502, and the anode 514 of the photodiode 510 is electrically connected to the emitter 508 of the transistor 502. Light 516 (produced by the scintillator 312 in response to x-ray radiation incident thereon, and/or ambient light) drives the photodiode 510, which drives the base 506 and hence the transistor 502. The transistor (i.e., emitter) current ($I_T$) is $\beta I_D$, where $I_D$ is the photodiode current and $\beta$ is the common-emitter gain of the transistor.

Figure 6:
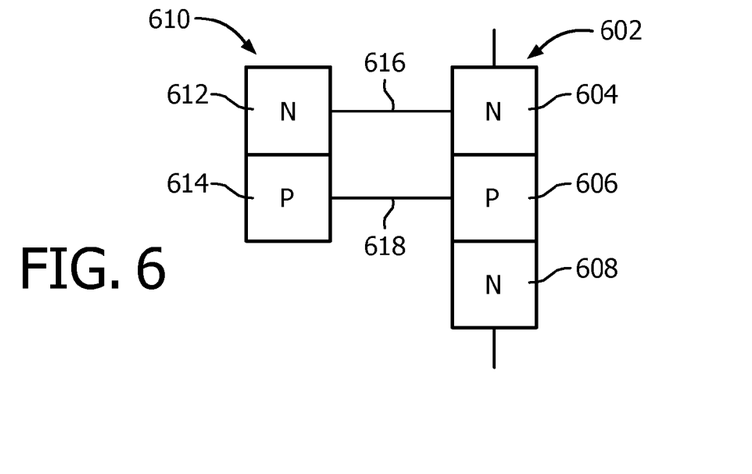
FIG. 6 schematically illustrates example semiconductors, representing the photo-transistor of FIG. 5, electrically connected through traces.

In FIG. 6, the photo-transistor 502 is represented through a first semiconductor 602, which in includes first N-type semiconductor material 604 (representing the collector), P-type semiconductor material 606 (representing the base), and second N-type semiconductor material 608 (representing the emitter). The photodiode 510 is represented through a second semiconductor 610, which in includes N-type semiconductor material 612 (representing the cathode) and P-type semiconductor material 614 (representing the anode). The cathode 612 is electrically connected to the collector 604 through a first electrical trace 616 in the silicon, and the anode 614 is electrically connected to the base 606 through a second electrical trace 618 in the silicon.

Figure 7:
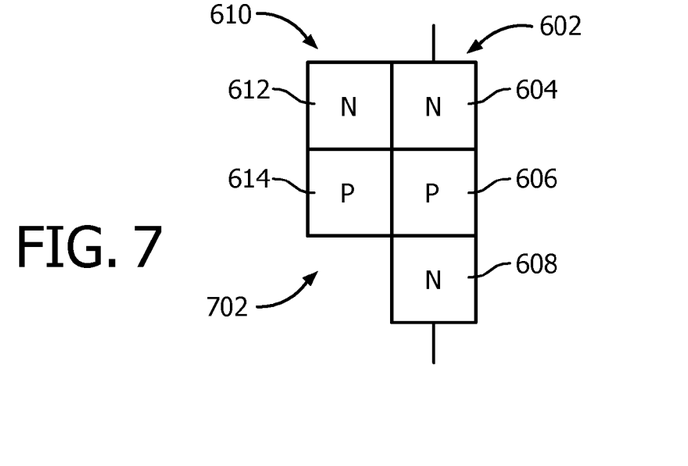
FIG. 7 schematically illustrates example semiconductors, representing the photo-transistor of FIG. 5, bonded or formed together.

FIG. 7 shows a variation of FIG. 6 in which the first semiconductor 602 and the second semiconductor 610 of FIG. 6 are joined, bonded, and/or combined into a single semiconductor 702.

Figure 8:
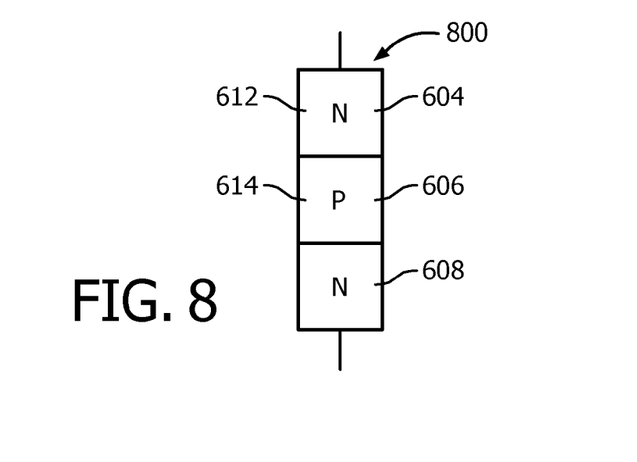
FIG. 8 schematically illustrates an example in which the photo-transistor of FIG. 5 is a single semiconductor element.

FIG. 8 shows an alternative representation of FIGS. 6 and 7 in which a single semiconductor 800 includes a first N-type semiconductor material 802 (which represents both the collector 604 and the cathode 612), a P-type semiconductor material 804 (which represents both the base 606 and the anode 614), and a second N-type semiconductor material 806 represents the emitter 608. In this configuration, the collector-base junction behaves like a photodiode, and can be configured with a geometry that increases an amount of light that is detected. The light causes an increased reverse leakage current across this junction, and this reverse leakage current has the same effect as current being supplied to the base.

Variations are discussed next.

The dark current produced by the photo-transistor 406 is a function of at least a temperature of the silicon detector tile 216. In the variation shown in FIG. 9, the photosensor area 304 further includes at least one temperature sensor 902. In one instance, the at least one temperature sensor 902 is part of and/or embedded in the silicon of the photosensor layer 302. A silicon detector tile 216 may include one or more such temperature sensors 902, within a photosensor area 304 (as shown), in a non-photosensitive area of the photosensor layer 302, between and/or overlapping at least two photosensor areas 304, etc.

Figure 9:
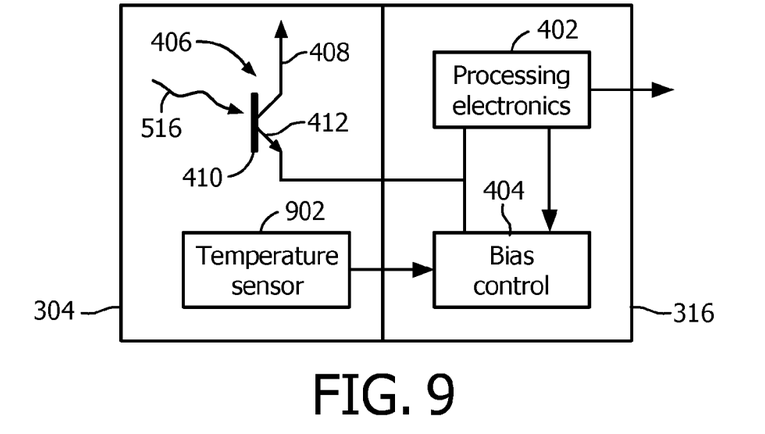
FIG. 9 schematically illustrates a variation of the single detector pixel/processing electronics pair of the detector tile of FIG. 3 that includes a thermal sensor in the silicon photosensor layer.

This can be variously implemented. For example, in one non-limiting instance, the at least one temperature sensor 902 is implemented as described in in U.S. application Ser. No. 12/853,349 to Luhta et al., filed on Aug. 10, 2010, and entitled "Imaging detector thermal control," the entirety of which is incorporated herein by reference. The at least one temperature sensor 902 conveys the sensed temperature to the bias control 404, which utilizes a pre-determined mapping between temperature and dark current to estimate a present amount of dark current and to control amount of dark current fed to the I/F converter based thereon. It may also be embedded in the electronics 316.

The dark current produced by the photo-transistor 406 can also vary with accumulated radiation dose deposited to the silicon detector tile 216. In the variation shown in FIG. 10, the photosensor area 304 further includes at least one radiation dose sensor 1002. In one instance, the at least one dose sensor 1002 is part of and/or embedded in the silicon of the photosensor 302. It may also be embedded in the electronics 316. A silicon detector tile 216 may include one or more such radiation dose sensors 1002, within a photosensor area 304 (as shown), in a non-photosensitive area of the photosensor layer 302, between and/or overlapping at least two photosensor areas 304, etc.

Figure 10:
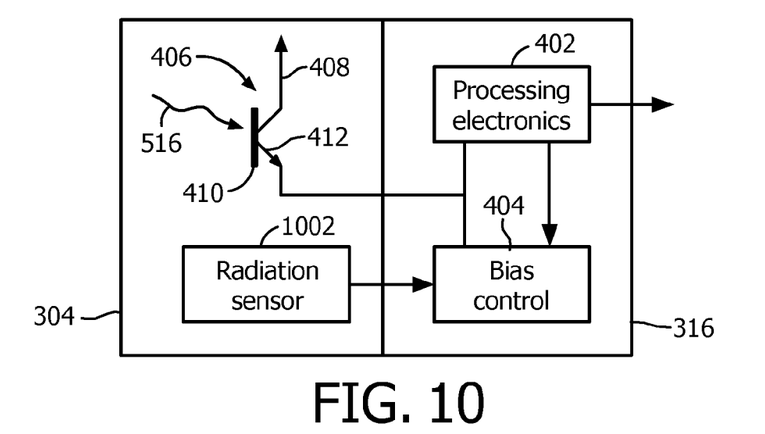
FIG. 10 schematically illustrates a variation of the single detector pixel/processing electronics pair of the detector tile of FIG. 3 that includes a radiation dose sensor in the silicon photosensor layer.

This can be variously implemented. For example, in one non-limiting instance, the at least one dose sensor 1002 is implemented as described in in U.S. application Ser. No. 13/510,168 to Chappo et al., filed on Nov. 18, 2010, and entitled "Radiation Dose Based Imaging Tile Parameter Compensation," the entirety of which is incorporated herein by reference. The at least one dose sensor 1002 conveys the sensed dose to the bias control logic 314, which utilizes a pre-determined mapping between dose and dark current to estimate a present amount of dark current and the control amount of dark current fed to the I/F converter based thereon.

In another variation, the silicon detector tile 216 includes both the at least one temperature sensor 902 and the at least one dose sensor 1002.

Figure 11:
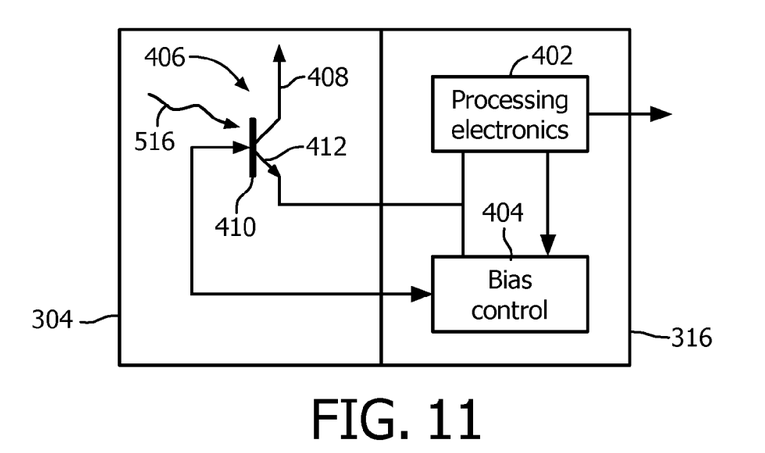
FIG. 11 schematically illustrates a variation of the single detector pixel/processing electronics pair of the detector tile of FIG. 3 in which the bias control logic controls a base current of the photo-transistor.

FIG. 11 shows a variation in which the bias control logic 404 also controls the base current of the photo-transistor 406. In this instance, the bias control logic 404 ensure that the base current is at a level which causes enough dark current to bias the I/F converter, including corrections for radiation dose and temperature.

Figure 12:
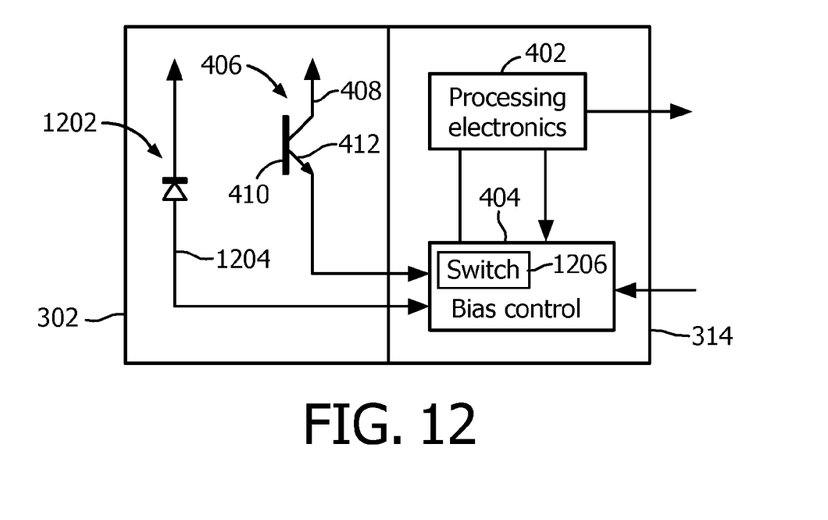
FIG. 12 schematically illustrates a variation of the single detector pixel/processing electronics pair of the detector tile of FIG. 3 with both a photodiode and a phototransistor in the silicon photosensor.

FIG. 12 shows a variation in which the photosensor 302 includes both the photo-transistor 406 and a photodiode 1202. In this instance, the emitter 412 of the photo-transistor 406 and an anode 1204 of the photodiode 1204 are in electrical communication with the bias control 404, which includes a switch 1206, which determines which of the emitter 412 or the anode 1204 is in electrical communication with the processing electronics 402. An input to the bias control 404 indicates which mode (photodiode or photo-transistor) the tile 216 is in. When in photodiode 1202 mode, the bias control 404 utilizes a current source (e.g., the current source 126 of FIG. 1) or the like to bias the I/F converter of the processing electronics 402.

Figure 13:
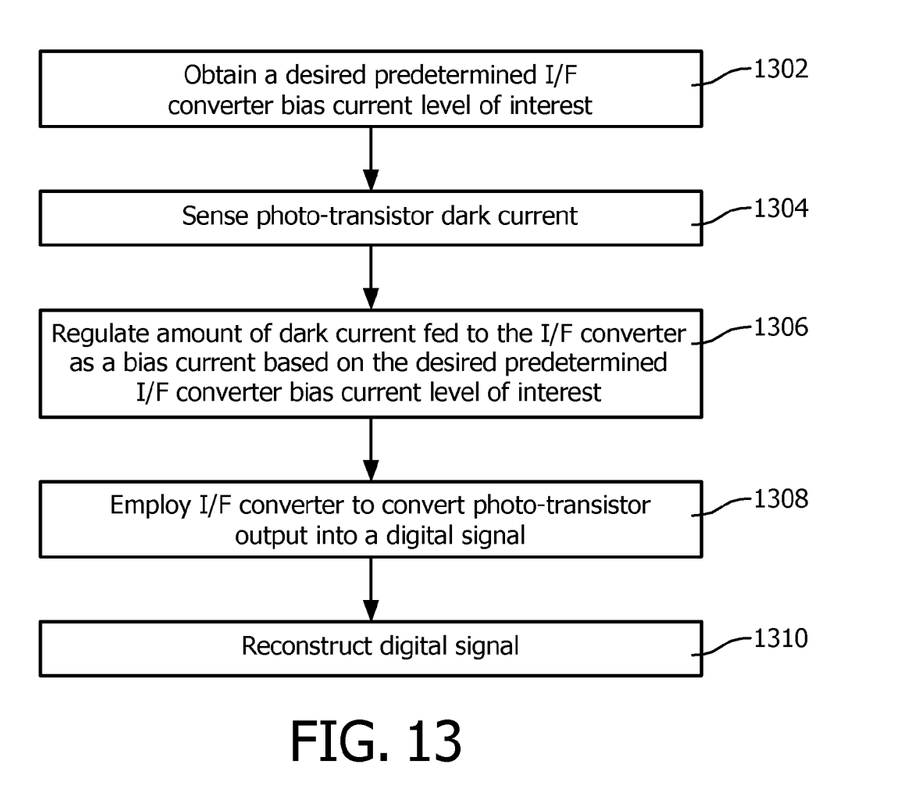
FIG. 13 illustrates an example method in accordance with the embodiments disclosed herein.

FIG. 13 illustrates a method in accordance with the embodiments discussed herein.

At 1302, a predefined bias current level of interest for an I/F converter that coverts a current output by the photo-transistor of a detector pixel of an imaging into a digital signal is obtained.

At 1304, a dark current of the photo-transistor is sensed.

At 1306, an amount of the dark current that is transmitted to the I/F converter is regulated at least based on the predefined bias current level.

As described herein, the amount of the dark current that is transmitted to the I/F converter may also be regulated based on a temperature and/or radiation dose deposited to the silicon detector tile 216.

At 1308, the I/F converter is employed to covert the output of the photo-transistor into a digital signal.

At 1310, the digital signal is reconstructed, generating volumetric image data.

It is to be appreciated that the ordering of the acts in the methods described herein is not limiting. As such, other orderings are contemplated herein. In addition, one or more acts may be omitted and/or one or more additional acts may be included.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A silicon imaging detector tile, comprising:
   a silicon photosensor layer including a plurality of detector pixels, each with a photo-transistor; and
   a silicon electronics layer, coupled to the silicon photosensor layer, including a current-to-frequency converter and bias control for each of the plurality of photo-transistors.

2. The silicon imaging detector tile of claim 1, wherein each of the plurality of photo-transistor produces a dark current, and a corresponding bias control regulates an amount of the dark current transmitted to a corresponding current-to-frequency converter.

3. The silicon imaging detector tile of claim 2, wherein the amount of the dark current transmitted to a corresponding current-to-frequency converter causes the current-to-frequency converter to produce at least one pulse within each integration period so that a frequency can be determined by the current-to-frequency converter.

4. The silicon imaging detector tile of claim 2, further comprising:
   a register that stores a value of an electrical current level required to causes the current-to-frequency converter to produce at least one pulse within each integration period, and the bias control employs the value to regulate the dark current.

5. The silicon imaging detector tile of claim 2, further comprising:
   a temperature sensor in the silicon photosensor layer that senses a temperature of the tile, wherein the bias control regulates the amount of the dark current transmitted to the corresponding current-to-frequency converter based on the sensed temperature.

6. The silicon imaging detector tile of claim 2, further comprising:
   a radiation sensor in the silicon photosensor layer that senses a radiation deposited to the tile, wherein the bias control regulates the amount of the dark current transmitted to the corresponding current-to-frequency converter based on the sensed radiation.

7. The silicon imaging detector tile of claim 2, wherein the bias control controls a base current of the photo-transistor.

8. The silicon imaging detector tile of claim 1, at least one of the detector pixels further includes a photo-diode, and wherein the bias control alternatively electrically connects the photodiode or the photo-transistor to the current-to-frequency converter.

9. The silicon imaging detector tile of claim 1, wherein the photo-transistor comprises at least two semiconductors connected together or a single semiconductor.

10. A method, comprising:
    sensing, with a photo-transistor of a detector pixel of a silicon photosensor layer of an imaging detector and in an absence of x-ray radiation, and producing a dark current;
    regulating, with bias control, an amount of the dark current transmitted to a current-to-frequency converter of a silicon electronics layer coupled to the silicon photosensor layer; and
    converting, with the current-to-frequency converter, the amount of the dark current transmitted to the current-to-frequency converter.

11. The method of claim 10, wherein the amount of the dark current transmitted to the corresponding current-to-frequency converter causes the current-to-frequency converter to produce at least one pulse within each integration period so that a frequency can be determined by the current-to-frequency converter.

12. The method of claim 11, further comprising:
    reading a register value of a register storing an electrical current level required to cause the current-to-frequency converter to produce at least one pulse within each integration period; and
    regulating the dark current based on the register value.

13. The method of claim 10, further comprising:
sensing a temperature of the silicon detector tile; and
further regulating the dark current based on the sensed temperature.

14. The method of claim 10, further comprising:
sensing a radiation deposited to the silicon detector tile; and
further regulating the dark current based on the sensed radiation.

15. The method of claim 10, further comprising:
controlling a base current of the photo-transistor to regulate the amount of dark current transmitted to the current-to-frequency converter.

16. The method detector of claim 10, wherein the detector pixel further includes a photo-diode; and further comprising:
selectively connecting one of the photodiode or the photo-transistor to the current-to-frequency converter.

17. An imaging system, comprising:
a radiation source that emits radiation;
a detector array that detects the radiation, the detector array including a plurality of detector tiles, each detector tile including a silicon photosensor layer with a plurality of detector pixels, each detector pixel including a photo-transistor; and a silicon electronics layer, coupled to the silicon photosensor layer, including a current-to-frequency converter and bias control for each of the plurality of photo-transistor, wherein the current-to-frequency converter converts a signal from the photo-transistor into a digital signal; and
a reconstructor that reconstructs the digital signal, generating volumetric image data.

18. The imaging system of claim 17, wherein a photo-transistor of a detector pixel produces a dark current, and a corresponding bias control regulates an amount of the dark current transmitted to a corresponding current-to-frequency converter, wherein the amount of the dark current transmitted to the corresponding current-to-frequency converter causes the current-to-frequency converter to produce at least one pulse within each integration period so that a frequency can be determined by the current-to-frequency converter.

19. The imaging system of claim 17, further comprising at least one temperature sensor in the silicon photosensor layer that senses a temperature of the tile, wherein the bias control regulates an amount of the dark current transmitted to the corresponding current-to-frequency converter based on the sensed temperature.

20. The imaging system of claim 17, further comprising at least one radiation sensor in the silicon photosensor layer that senses a radiation deposited to the tile, wherein the bias control regulates an amount of the dark current transmitted to the corresponding current-to-frequency converter based on the sensed radiation.

21. The imaging system of claim 17, wherein the bias control for a photo-transistor controls a base current of the photo-transistor.

22. The imaging system of claim 17, wherein at least one of the detector pixels also includes a photo-diode, and the bias control electrically connects either the photodiode or the photo-transistor to the current-to-frequency converter, and the bias control utilizes a current source to bias the current-to-frequency converter of the processing electronics.

23. The imaging system of claim 17, wherein the detector pixels are photon counting detector pixels.

* * * * *